United States Patent
Kwon et al.

(10) Patent No.: US 11,154,187 B2
(45) Date of Patent: Oct. 26, 2021

(54) APPARATUS AND METHOD FOR IN VIVO CLEANING OF AN OPTICAL LENS OF A SURGICAL VISUALIZATION DEVICE

(71) Applicants: Peter H. Kwon, Middletown, NY (US); James L. Levinsohn, Middletown, NY (US); Jeffrey Ralph Swift, Boca Grande, FL (US)

(72) Inventors: Peter H. Kwon, Middletown, NY (US); James L. Levinsohn, Middletown, NY (US); Jeffrey Ralph Swift, Boca Grande, FL (US)

( * ) Notice: Subject to any disclaimer, the term of this patent is extended or adjusted under 35 U.S.C. 154(b) by 0 days.

(21) Appl. No.: 16/819,483

(22) Filed: Mar. 16, 2020

(65) Prior Publication Data
US 2020/0375443 A1 Dec. 3, 2020

Related U.S. Application Data

(60) Provisional application No. 62/853,920, filed on May 29, 2019.

(51) Int. Cl.
*A61B 1/12* (2006.01)
*A61B 1/005* (2006.01)
*A61B 1/00* (2006.01)
*A61B 1/06* (2006.01)

(52) U.S. Cl.
CPC .......... *A61B 1/122* (2013.01); *A61B 1/0051* (2013.01); *A61B 1/00066* (2013.01); *A61B 1/00087* (2013.01); *A61B 1/0676* (2013.01); *A61B 1/126* (2013.01); *A61B 1/127* (2013.01)

(58) Field of Classification Search
CPC ........ A61B 1/126–127; A61B 1/00098; A61B 1/0058
USPC ......................................... 600/106–107, 151
See application file for complete search history.

(56) References Cited

U.S. PATENT DOCUMENTS

| | | | |
|---|---|---|---|
| 4,742,817 A * | 5/1988 | Kawashima | A61B 1/0052 600/104 |
| 5,295,952 A | 3/1994 | Pietrafitta | |
| 5,313,934 A | 5/1994 | Wiita et al. | |
| 5,382,297 A | 1/1995 | Valentine et al. | |
| 5,392,766 A * | 2/1995 | Masterson | A61B 1/0008 15/244.1 |
| 5,400,767 A | 3/1995 | Murdoch | |
| 5,464,008 A | 11/1995 | Kim | |
| 5,514,084 A * | 5/1996 | Fisher | A61B 1/126 600/157 |
| 5,518,502 A * | 5/1996 | Kaplan | A61B 1/126 600/156 |
| 5,647,840 A | 7/1997 | D'Amelio et al. | |
| 6,354,992 B1 | 3/2002 | Kato | |
| 6,406,425 B1 | 6/2002 | Chin et al. | |

(Continued)

*Primary Examiner* — Matthew J Kasztejna
(74) *Attorney, Agent, or Firm* — Cowan, Liebowitz & Latman, P.C.; Anastasia Zhadina (57) ABSTRACT

A surgical device comprising a shaft having a proximal end and a distal end, a spring extending from the distal end of the shaft and curving away from a longitudinal axis of the shaft, the spring having a predetermined width and a thickness substantially smaller than the predetermined width to provide preferential bending in a direction of the curvature of the spring, and a tip extending from a distal end of the spring, said tip including an attachment surface for attaching an absorbent material thereto.

31 Claims, 8 Drawing Sheets

(56) References Cited

U.S. PATENT DOCUMENTS

| | | | |
|---|---|---|---|
| 6,447,444 B1* | 9/2002 | Avni | A61B 1/31 600/121 |
| 7,918,783 B2* | 4/2011 | Maseda | A61B 1/018 600/104 |
| 8,267,896 B2 | 9/2012 | Hartoumbekis et al. | |
| 8,289,381 B2* | 10/2012 | Bayer | A61B 1/0051 348/65 |
| 8,517,977 B2 | 8/2013 | Taylor et al. | |
| 8,550,988 B2 | 10/2013 | Pribanic | |
| 8,668,642 B2 | 3/2014 | Kleyman | |
| 8,690,764 B2* | 4/2014 | Clark | A61B 1/00135 600/157 |
| 8,752,230 B2 | 6/2014 | Brand et al. | |
| 9,050,036 B2 | 6/2015 | Poll et al. | |
| 9,232,935 B2* | 1/2016 | Brand | A61B 1/126 |
| 9,241,613 B2 | 1/2016 | Hsu et al. | |
| 9,486,129 B2* | 11/2016 | Rodriguez Sanjuan | B08B 9/04 |
| 9,526,409 B2 | 12/2016 | Gomez et al. | |
| 9,545,194 B2 | 1/2017 | Nguyen | |
| 9,775,502 B2 | 10/2017 | Miller et al. | |
| 10,264,957 B2 | 4/2019 | Yoshida et al. | |
| 10,791,918 B1* | 10/2020 | Gilkey | A61B 1/126 |
| 2002/0022762 A1 | 2/2002 | Beane et al. | |
| 2004/0199088 A1* | 10/2004 | Bakos | A61M 25/09 600/585 |
| 2006/0135848 A1* | 6/2006 | Koch | A61B 1/0058 600/104 |
| 2006/0293559 A1 | 12/2006 | Grice, III et al. | |
| 2009/0105543 A1* | 4/2009 | Miller | A61B 1/122 600/155 |
| 2012/0071717 A1 | 3/2012 | Podolski et al. | |
| 2013/0053639 A1 | 2/2013 | Ihde, II | |
| 2013/0085337 A1* | 4/2013 | Hess | A61B 1/126 600/157 |
| 2013/0305469 A1 | 11/2013 | Rodriguez Sanjuan | |
| 2014/0034082 A1 | 2/2014 | Hurst et al. | |
| 2016/0113484 A1 | 4/2016 | Nakaguchi | |
| 2016/0166135 A1 | 6/2016 | Fiset | |
| 2016/0175065 A1 | 6/2016 | Gomez et al. | |
| 2016/0360955 A1* | 12/2016 | Georgian | A61B 90/70 |
| 2018/0116496 A1* | 5/2018 | Arcot | A61B 1/00135 |
| 2018/0256019 A1 | 9/2018 | Rosenbaum et al. | |
| 2018/0306049 A1 | 12/2018 | Rosenbaum et al. | |
| 2018/0344141 A1* | 12/2018 | Rosenbaum | A61B 1/00089 |
| 2019/0059713 A1 | 2/2019 | Allen et al. | |
| 2019/0110674 A1 | 4/2019 | Allen et al. | |

* cited by examiner

APPARATUS AND METHOD FOR IN VIVO CLEANING OF AN OPTICAL LENS OF A SURGICAL VISUALIZATION DEVICE

BACKGROUND OF THE INVENTION

The present invention relates to endoscopic surgical procedures, and more particularly to apparatus and methods for maintaining visibility of the Surgical field through the endoscope.

During endoscopic surgery a device called a trocar is pierced through the patient's skin. The Trocar commonly contains an internal flap that is initially closed and prevents fluids and gasses from escaping from the patient. A laparoscope or endoscope is inserted through the trocar, and the trocar internal flap will seal around the endoscope to prevent fluids and gasses from escaping the patient. During surgery several trocars may be inserted so that different instruments can be inserted into the patient simultaneously. Carbon Dioxide is often injected into the patient to create an internal cavity. This gas filled cavity improves the physician's ability to see the operating field through the endoscope.

During endoscopic surgery, the tip of the endoscope often gets fogged or compromised by body fluids or blood, resulting in poor visualization of the surgical field. According to present methods, this requires frequent withdrawal of the endoscope from the patient to clean the tip, ex vivo.

The ex vivo solutions work reasonably well, but requires the withdrawal of the endoscope to clean the tip. This results in prolongation of operative time, while losing visualization throughout the procedure.

Existing in vivo solutions may work, but require additional tubing and connections, and are costly.

For example, prior art that disclose performing endoscope tip cleaning in vivo are disclosed include Brand et al U.S. Pat. No. 8,252,330B2 and Ihde US 213/0053639 A1. However, these solutions each require complex assemblies to hold, manipulate, and deploy a cleaning surface in vivo. The complexity and cost of these devices diminishes their effectiveness.

Ex vivo endoscope cleaning devices span a range of complexity from a simple sponge soaked with an anti-fog liquid to an instrument that contains a soaked sponge and tip heater. The tip heater helps prevent condensation when an endoscope tip is allowed to cool ex vivo and then is reinserted into a patient cavity that contains high humidity. However, these cleaning devices require the endoscope to be removed and reinserted into the patient cavity, interrupting visualization of the operative field.

SUMMARY OF THE INVENTION

The present invention is directed to an improved apparatus and methods that can effectively clean the tip of the endoscope or laparoscope in vivo, without need for additional tubing or connections, eliminating the need to withdraw the laparoscope, maintaining full visualization of the operative field, and therefore, increasing patient safety while reducing operative time.

The in vivo endoscope cleaning device of the present invention has the simplicity and cost similar to an ex vivo liquid soaked sponge, but eliminates the need for tip heating and endoscope removal from the patient.

In one instance, a device is described that comprises a handle at the proximal end, a rod projecting from the handle toward the distal end, a curved spring structure projecting from the rod, and an element projecting from the end of the curved spring, such element containing an open cavity where a sponge or other cleaning surface is attached. The spring is configured to deform in a preferred direction during the insertion of the device through a trocar channel. After insertion through the trocar channel the spring will return to its original curvature and thus position the sponge at an angle suitable for contact with an endoscope tip protruding from a second trocar. Such endoscope tip to have easy and direct access to the sponge for tip cleaning purposes. After cleaning the device may remain in vivo for subsequent endoscope tip cleaning, may be removed to clean the sponge, or may be removed and replaced. In all cases the endoscope can remain in vivo in a fully functional state for the purposes of the surgical procedure.

In another instance, the device may be made from a single molded plastic piece coupled to a sponge. In this instance the required properties of the spring are satisfied by suitable design and selection of biocompatible plastic materials and spring structure requirements.

In another instance, the sponge may have a green, or other contrasting color to the patient cavity color. This color contrast aids the physician to locate the sponge in vivo while the endoscope tip may be contaminated and thus have significantly reduced visibility.

In another instance, the device may be made of a translucent or transparent material and may contain a light source which illuminates the distal end containing the sponge. This illumination will cause the features holding the sponge to light up and will produce a glowing area surrounding the sponge. This glowing area may facilitate the physician locating the sponge in vivo when the endoscope viewing tip is contaminated and obscures visibility.

In another instance, the device may have a protrusion from the handle in a second direction opposite to the distal end. This protrusion may have a cleaning surface suitable for cleaning the inside sealing flap of a trocar. Trocars often transfer contamination to instruments during insertion and often require cleaning to prevent endoscope tip or other instrument contamination.

The present invention is directed to surgical device comprising: a shaft having a proximal end and a distal end, a spring extending from the distal end of the shaft and curving away from a longitudinal axis of the shaft, the spring having a predetermined width and a thickness substantially smaller than the predetermined width to provide preferential bending in a direction normal to the longitudinal axis of the shaft and specifically, in a direction of the curvature of the spring, and a tip extending from a distal end of the spring, said tip including an attachment surface for attaching an absorbent material thereto. The present invention is also directed to a surgical device comprising a shaft having a proximal end and a distal end, a spring extending from the distal end of the shaft and curving from 40 to 90 degrees away from a longitudinal axis of the shaft, and a tip extending from a distal end of the spring, said tip having an attachment surface for attaching an absorbent material thereto, wherein, when the surgical device is inserted through a trocar, the spring independently deforms from an initial curved position to a second position that is colinear to an insertion channel in the trocar.

In some embodiments, the surgical device includes the absorbent material configured to attach to the attachment surface of the tip, wherein the absorbent material comprises one of a sponge, a cloth, a cleaning pad and a plastic foam. The surgical device may also include a handle, wherein the proximal end of the shaft extends from the handle.

In some embodiments, the tip of the surgical device is configured so as to reduce insertion and removal impediments caused by temporary interfacing between the tip and sharp features of a trocar. Specifically, the tip includes a conical distal end, one or more ramps providing a smooth transition between the spring and a body of the tip, and a recess in the body of the tip, said attachment surface being provided in said recess.

In some embodiments, the tip, the spring, the shaft and/or the handle are integrally formed into a single structure. The single structure may be molded from a biocompatible plastic. In certain embodiments, the surgical device further includes an illumination assembly at least partially housed within the handle, with the illumination assembly being configured to provide light to the tip through the shaft and the spring via total internal reflection. In some embodiments, the absorbent material has a contrasting color to a patient surgical cavity.

In certain embodiments, the surgical device also comprises a second shaft attached to the proximal end of the surgical device, and a second absorbent material attached to a free end of the second shaft.

A method of wiping an endoscope tip inside a human body is also described. The method comprises inserting a surgical device into the human body via an incision, the surgical device comprising a shaft, a spring extending from a distal end of the shaft and curving away from a longitudinal axis of the shaft, a tip extending from the distal end of the spring and including an attachment surface, and an absorbent material attached to the attachment surface of the tip, manipulating the surgical device so that the absorbent material attached to the tip of the surgical device comes into contact with the endoscope tip, and applying pressure to the endoscope tip using the tip of the surgical device so as to wipe the endoscope tip using the absorbent material. The inserting step comprises flexing the spring of the surgical device so that the spring is substantially aligned with the longitudinal axis of the shaft and inserting at least the tip and the spring of the surgical device through a trocar inserted into the human body at a predetermined distance from the endoscope, and after the surgical device is inserted into the human body, the spring returns to a relaxed state curving away from the longitudinal axis of the shaft.

In certain embodiments, a proximal end of the shaft is attached to a handle and the step of manipulating is performed by manipulating the handle. In some embodiments, the surgical device also includes an illumination assembly configured to provide light to the tip of the surgical device, and the method further comprises illuminating the tip of the surgical device to enhance visibility of the tip in the human body.

In some embodiments, the method also includes attaching the absorbent material to the attachment surface of the tip prior to the inserting step. In addition, the method may include a step of applying cleaning solution to the absorbent material, said step of applying is performed one of (a) ex vivo prior to the inserting step, and (b) in vivo after the inserting step. The method further includes removing the surgical device from the human body by passing at least the spring and the tip of the surgical device through the trocar to the outside of the body, wherein during the removing step, the spring is flexed to be substantially aligned with the longitudinal axis of the shaft.

BRIEF DESCRIPTION OF THE DRAWINGS

The above and other features of the invention are shown in the following figures.

DETAILED DESCRIPTION OF THE INVENTION

The following detailed description is of exemplary embodiments of the invention. The description is not to be taken in a limiting sense, but is made merely for the purpose of illustrating the general principles of the invention. Broadly, embodiments of the present invention provide a system method and apparatus for in vivo cleaning a lens of an endoscope.

FIGS. 1A-2A and 2C-2D show an exemplary embodiment of an endoscope lens cleaning apparatus 100 according to aspects of the invention. The apparatus 100 includes an elongate rod or shaft (102) having a handle (130) at a proximal end and a flexible spring (120) and a cleaning tip (110) at a distal end thereof. The handle 130, in the present embodiment, has a longitudinal axis substantially aligned with longitudinal axis of the elongate rod (102). However, in other embodiments, the handle (130) may extend from the elongate rod (102) at an angle. In addition, in FIGS. 1A-2A and 2C-2D, the handle (130) has a substantially cylindrical shape and is greater in circumference than the elongate rod (102). In other embodiments, the shape and size of the handle (130) may be varied. For example, the size and shape of the handle (130) may be adjusted when the handle houses therein at least a portion of an illumination assembly as described below. The handle (130) is utilized to manipulate the apparatus in order to insert, retract, and clean the endoscope or laparoscope lens in vivo.

The elongate rod (102), the flexible spring (120) and the cleaning tip (110) of the apparatus (100) are dimensioned so as to be able to pass through a channel in a standard trocar. Specifically, the elongate rod (102) is of a sufficient width to fit within a trocar channel and to ensure adequate fluidic or gaseous sealing by the trocar. Similarly, the spring (120) has sufficient width to fit within the trocar channel. For example, the widest portion of the elongate rod (102), the flexible spring (120) and the cleaning tip (110) preferably is equal to or smaller than 12 mm. The length of the elongate rod (102) is sufficient to protrude simultaneously through a proximal end and a distal end of the standard trocar when inserted into the trocar channel. For example, the length of the elongate rod (102) is between 20 cm and 60 cm.

Figure 1A:
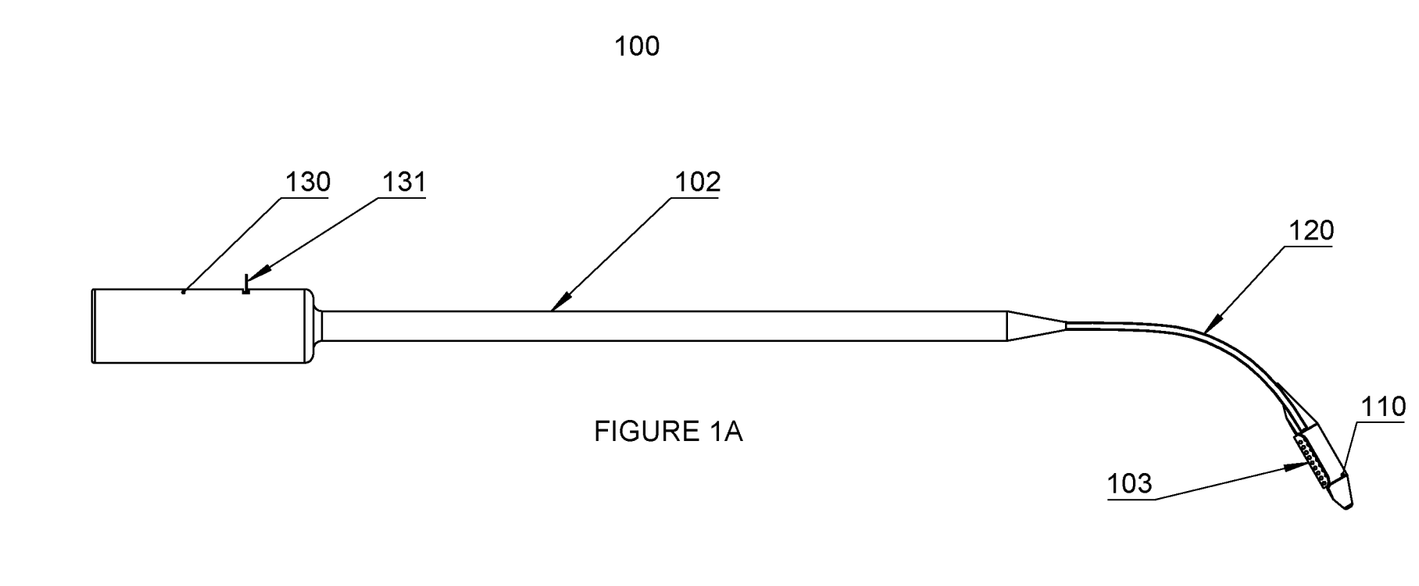
FIG. 1A is a side view of the endoscope lens cleaning apparatus in a relaxed retracted position.
Figure 1B:
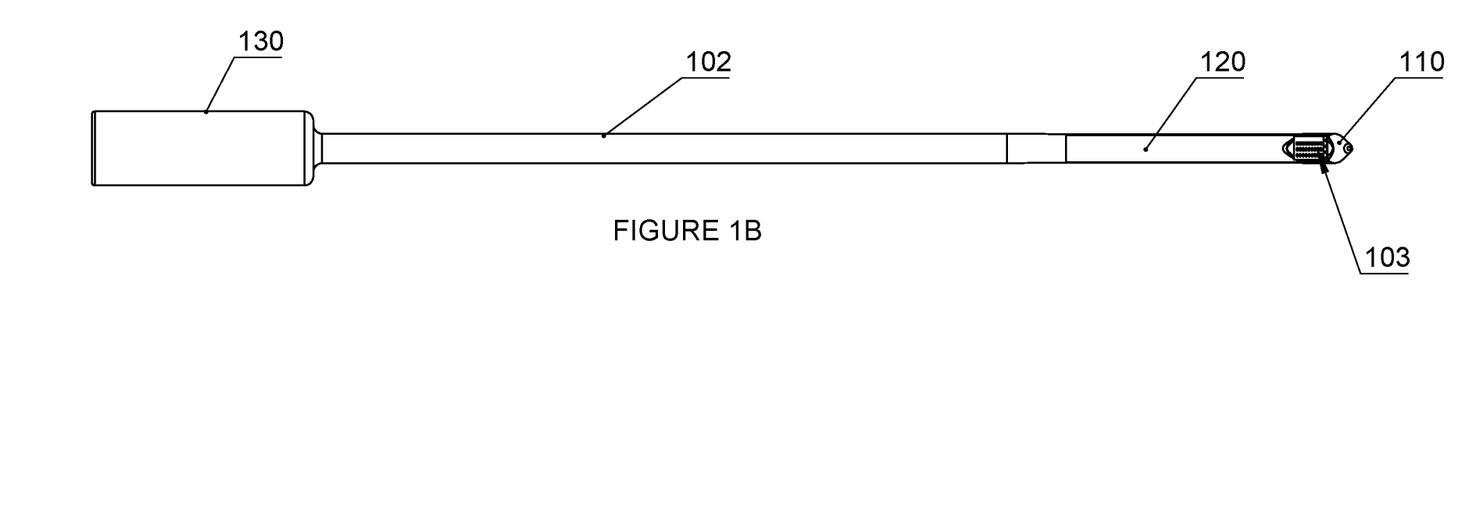
FIG. 1B is a bottom view of the endoscope lens cleaning apparatus in a relaxed retracted position.

In addition, in order to facilitate insertion and removal the endoscope lens cleaning apparatus (100) through a standard trocar, the elongate rod (102), the flexible spring (120) and the cleaning tip (110) have smooth or gradual transitions between portions of varying thickness. In this way, sharp and stepped edges that could get caught on portions of the trocar or may damage tissues are eliminated. For example, as can be seen in FIG. 1A, since the thickness of the flexible spring (120) is smaller than the thickness of the elongate rod (102), the distal edge of the elongate rod (102) gradually narrows to the thickness of the flexible spring (120). As can be seen in FIG. 1B, since the width of the flexible spring (120) in this exemplary embodiment is similar to the width of the elongate rod (102), the width of the elongate rod (102) at the distal end remains substantially the same. However, if the width of the flexible spring (120) is modified to be smaller than the width of the elongate rod (102), then the width of the elongate rod (102) may be modified to gradually decrease at the distal end. As also shown in FIGS. 1A-1B and described in more detail below, the cleaning tip 110 has a tapered distal end and the proximal end of the cleaning tip (110) tapers in thickness or height to the thickness of the flexible spring (120).

Figures 2A, 2B:
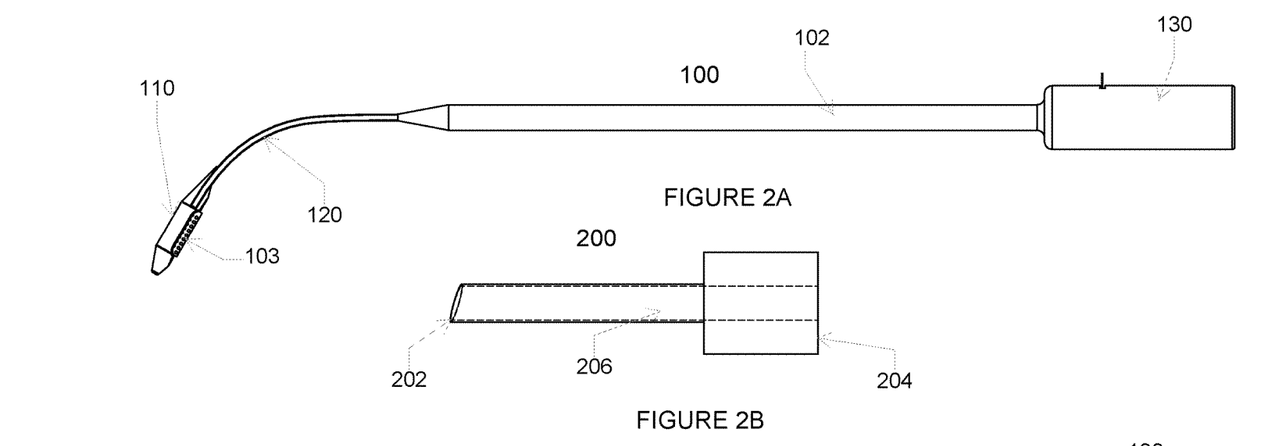
FIG. 2A is another side view of the endoscope lens cleaning apparatus in a relaxed retracted position.
FIG. 2B shows a Trocar insertion tool for use with the endoscope lens cleaning apparatus of FIGS. 1A-2A.
Figure 2C:
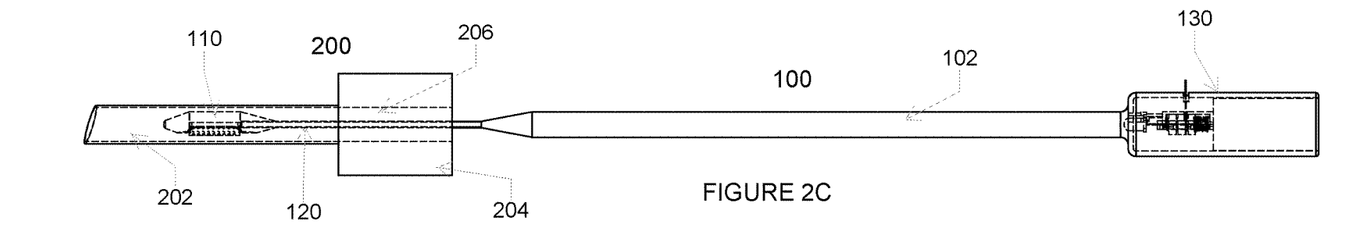
FIG. 2C shows the endoscope lens cleaning apparatus of FIGS. 1A-2A being inserted through a trocar, such apparatus non-permanently deformed into a shape colinear with the trocar, such that it can travel through the trocar unimpeded.

As shown in FIGS. 1A-2A and 2C-2D, the cleaning tip (110) includes an attachment surface for attachment of a cleaning pad or an absorbent material (103). In FIGS. 1A-2A and 2C-2D, the cleaning tip (110) has the cleaning pad (103), which may be a sponge, a cloth, a wipe, an optical cleaning pad, a suitable absorbent material or any other suitable cleaning materials. As also shown in FIGS. 1A-2A an 2C-2D, the cleaning tip (110) is formed at the distal end such that the cleaning tip is oriented at an angle of 40-90 degrees to a longitudinal axis of the apparatus in a relaxed state. The cleaning tip (100) is attached to a distal end of the resiliently deformable spring (120), which is attached to the elongate rod (102). As shown in FIG. 2C, the tip (110) may be flexed to substantially align with the longitudinal axis of the apparatus when the tip (110) is flexed to a tensioned condition. The tip (110) may also be flexed to different angles, either greater or smaller than the angle of the tip (110) in a relaxed state, which allows for flexibility when cleaning the endoscope or laparoscope tip.

As shown, the cleaning pad or absorbent material (103), such as an optical cleaning pad, a sponge, cloth, plastic foam, or wipe, is affixed to the cleaning tip (110) and in particular, to the attachment surface of the cleaning tip (110). A cleaning solution may be applied to the cleaning pad or surface (103). Preferably, the cleaning solution has anti-fog properties. During endoscopic surgery, the tip of the endoscope or laparoscope often gets fogged or compromised by body fluids or blood, resulting in poor visualization and frequent withdrawal of the endoscope to clean the tip. The apparatus of the present invention can be introduced through a secondary trocar to clean the endoscope, thereby avoiding the need for the withdrawal and reinsertion of the endoscope, reducing operative times and poor visualization.

The cleaning pad (103) is firmly attached to the cleaning tip (110) with an adhesive, or an attachment clip or any other suitable fastener. For example, the cleaning pad (103) may be attached to the cleaning tip (110) with glue, epoxy, UV Cure, or other suitable biocompatible attachment methods. In certain embodiments, the cleaning pad (103) is permanently and non-releasably/non-removably attached to the cleaning tip (110). In other embodiments, the cleaning pad (103) is releasably attached to the cleaning tip (110) and may be interchanged with other cleaning pads, if needed. The anti-fog solution is applied to the cleaning pad (103) to eliminate the fogging while also assisting in cleaning the optical tip of the endoscope. In some embodiments, the anti-fog solution is pre-applied to the cleaning pad (103) before the apparatus (100) is inserted through the trocar. In other embodiments, the anti-fog solution may be stored or held within the cleaning tip (110), or supplied to the cleaning tip (110), and applied to the cleaning pad (103) as needed during use, such as by a user operation, or when sufficient external pressure is applied to the cleaning pad (103). For example, an activation device, such as a button or a switch, may be provided in the handle or in the elongate rod (102) of the apparatus to allow the user to activate application of the cleaning solution or anti-fog cleaning solution to the cleaning pad (103). Alternatively, application of pressure to the cleaning pad (103), such as when the cleaning pad (103) presses against an endoscope tip, causes application of a predetermined amount of anti-fog cleaning solution to the cleaning pad (103) from the cleaning tip (110).

The cleaning tip (110) will allow for cleaning a variety of angles to the endoscope tip, due to its flexibility. Specifically, since the cleaning tip (110) is connected to the spring (120), the cleaning tip (110) can be moved to different angles relative to the endoscope tip. Also, due to the flexing of the spring (120) during cleaning, a small amount of pressure is applied by the cleaning tip (110) to the endoscope tip so as to allow for cleaning off any debris and body fluids from the endoscope tip without damaging the endoscope lens.

Figure 2D:
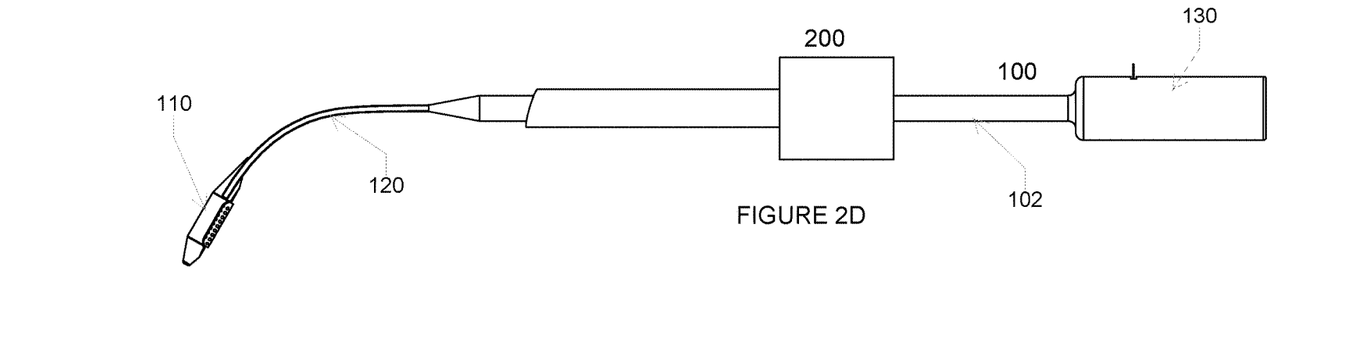
FIG. 2D shows the endoscope lens cleaning apparatus of FIGS. 1A-2A and 2C after insertion through a trocar and in a relaxed deployed position within the abdominal cavity.

FIG. 2B shows an exemplary trocar (200) that may be used with the endoscope lens cleaning apparatus (100) of the present invention. As shown, the trocar (200) includes an insertion tip or in vivo end (202), which is inserted into a body cavity through an incision, an ex vivo end (204), which remains outside the body and forms a seal between the body cavity and the outside, and a channel or guide tube (206) extending between the ex vivo end (204) and the in vivo end (202). FIGS. 2C and 2D show insertion of the endoscope lens cleaning apparatus (100) through the trocar (200) of FIG. 2B. It is understood that other types of trocars and/or access devices may be used with the endoscope lens cleaning apparatus (100).

FIG. 2C shows that the cleaning tip (110) and spring (120) may be flexed to a tensioned condition for insertion into the ex vivo end (204) of the secondary trocar guide tube (206). As shown, the cleaning tip (103) and the spring (120) are flexed to substantially follow the channel or guide tube (206) of the trocar (200) during the insertion. FIG. 2D shows the endoscope lens cleaning apparatus (100) after the cleaning tip (110) and the spring (120) clear the in vivo end (204) of the trocar tube (200), such that the cleaning tip (110) and the spring (120) return to their relaxed state that is angled relative to the longitudinal axis of the trocar (200) and to the longitudinal axis of the elongated rod (102). The surgeon, or surgical assistant can then manipulate the handle (130) to wipe the optical lens of the endoscope using the cleaning tip (110) of the apparatus (100).

Figures 3A, 3B:
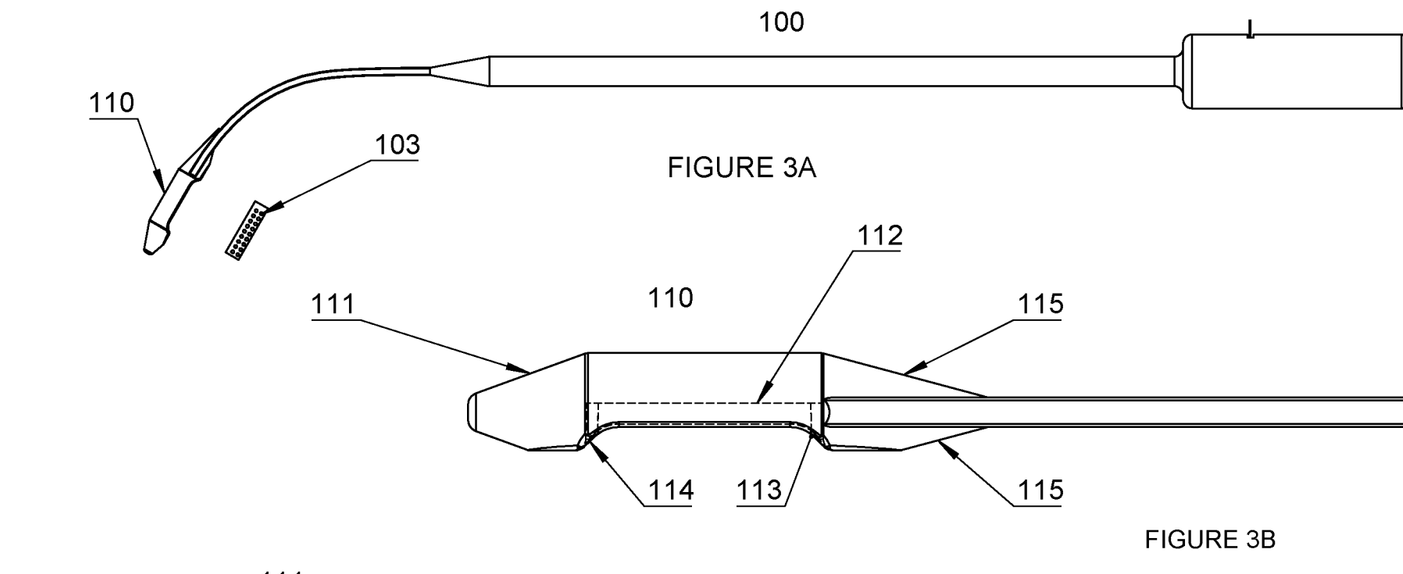
FIG. 3A shows the endoscope lens cleaning apparatus showing the location of the sponge cavity with the sponge removed for clarity.
FIG. 3B is a detailed side view of the sponge cavity.
Figure 3C:
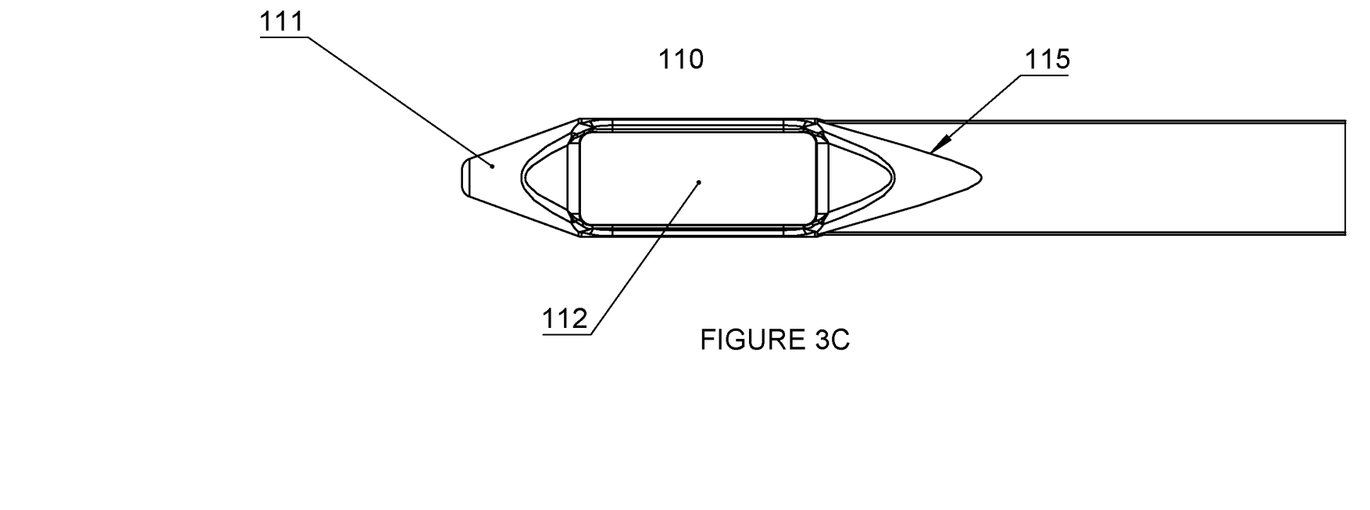
FIG. 3C is a detailed bottom view of the sponge cavity.

FIGS. 3A-3C show, in more detail, the cleaning tip (110) of the endoscope lens cleaning apparatus (100). In FIG. 3A, the apparatus (100) is shown with the cleaning pad (103) removed from the cleaning tip (110), while FIGS. 3B and 3C show enlarged views of the cleaning tip (110) without the cleaning pad attached thereto. As shown in FIG. 3A, in the relaxed state of the apparatus (100), the cleaning tip (110) is angled relative to the longitudinal axis of the apparatus (100) and includes a recessed area (112) on a first surface thereof. The cleaning pad (103) attaches to and covers the recessed area (112) of the cleaning tip (110). As shown in FIG. 3A, the first surface with the recessed area (112) faces generally in the same direction as a concave surface of the spring (120).

FIG. 3B shows an enlarged side view of the cleaning tip (110) without the cleaning pad (103) attached thereto and the details of the tip cavity or recessed area (112) which holds the sponge, or another tip cleaning surface (103). In FIGS. 3B and 3C, features necessary for easy trocar insertion and withdrawal are illustrated. As described in more detail below, the features of the cleaning tip (110) reduce insertion and removal impediments caused by temporary interfacing between the features of the cleaning tip (110) and sharp edges of the trocar when the apparatus (100) is inserted into the trocar channel. These features, which are described below, are perpendicular to the cleaning tip axis and provide smooth transitioning between the surfaces of the cleaning tip (110) and the surfaces of the trocar.

As shown, the cleaning tip (110) has a tapered or cone like structure (111) at its distal end to facilitate insertion of the cleaning tip (110) into the internal Trocar tube structure. The recessed area (112) is provided on one side, i.e., the first surface, of the cleaning tip (110) and as shown by the dashed lines in FIG. 3B, extends into a cavity within the cleaning tip (110) partially surrounded by the sidewalls of the cleaning tip (110). The depth of the cavity of the recessed area (112) is about 2-3 mm, but may vary depending on the cleaning pad (103) used and the way the cleaning pad (103) is attached to the cleaning tip (110). Moreover, the depth of the cavity of the recessed area (112) may be greater in a case that anti-fog cleaning solution is stored within the cleaning tip (110).

As shown in FIG. 3C, the recessed area (112) is substantially rectangular in shape so as to correspond to the shape of the cleaning pad (103). However, in other embodiments, the shape of the recessed area (112) may be varied depending on the shape and type of cleaning pad (103) used and how the cleaning pad (103) attaches to the cleaning tip (110).

Moreover, as can be seen in FIGS. 3B and 3C, the sidewalls of the cleaning tip (110) defining the proximal and distal ends of the recessed area (112) are curved, forming a proximal curved structure (113) and a distal curved structure (114). These curved structures (113, 114) provide smooth transitions between the recessed area (112) and the walls of the cleaning tip (110) outside of the recessed area (112). Furthermore, as can be seen in FIG. 3B, the sidewalls adjacent the curved structures (113, 114) may be beveled. As shown in FIGS. 3B and 3C, the proximal end of the cleaning tip (110) has ramped structures (115) on the first surface of the cleaning tip (110) and on a second surface of the cleaning tip (110) opposing the first surface. These ramped structures (115) taper the proximal end of the cleaning tip (110) to a thickness similar to that of the spring (120) and partially enclose the distal end of the spring (120).

The recessed area (112) in the cleaning tip (110) holds and protects the sponge (103) during insertion through the Trocar when spring tension forces press the sponge surface against the internal structures of the Trocar. When the cleaning tip (110) passes within the tube or channel of the trocar, the sponge (103) may be positioned within the cavity of the recessed area (112) so that does not protrude from the cleaning tip (110) in order to avoid damage thereto and to prevent removal of the sponge (103) from the cleaning tip. As the cleaning tip (110) emerges from the trocar in vivo, the curved structure (113) prevents the cleaning tip from being impeded by the in vivo rim of the Trocar tube as a result of spring tension. Similarly, the curved structure (114) prevents the cleaning tip (110) from being impeded by the in vivo rim of the Trocar tube during extraction of the apparatus (100). Similarly, the ramp structures (115) also prevent the cleaning tip (110) from being impeded by the in vivo rim of the Trocar tube during extraction of the apparatus (100).

During extraction of the apparatus (100) through a Trocar, device spring tension will be created by the straight tubular structure of the Trocar that forces the spring (120) to temporarily straighten to conform to the axial structure of the Trocar tube. This spring force will push the tip of the device against a preferred side of the Trocar tube. Sharp edges on this side of the Trocar tube (i.e. the distal tip of the trocar where the inside tube of the Trocar stops) can catch on device tip structures, and thus, the ramp structures (115) and the curved edge structure (114) are added to eliminate device extraction hinderances, and the cone structure (111) and curved edge structure (113) are added to eliminate device insertion hinderances.

Figures 4A, 4B:
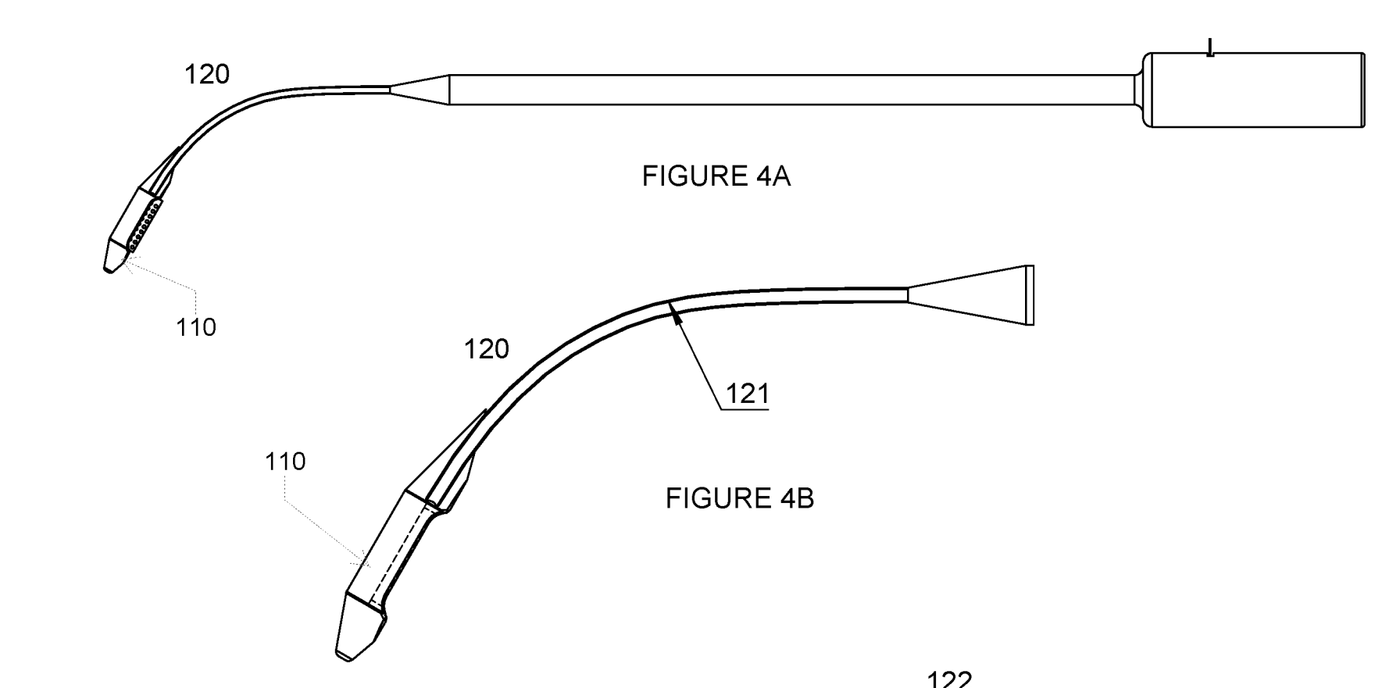
FIG. 4A is a side view of the endoscope lens cleaning apparatus showing the location of the spring portion of the device.
FIG. 4B shows a detailed side view of the spring portion of the device.
Figure 4C:
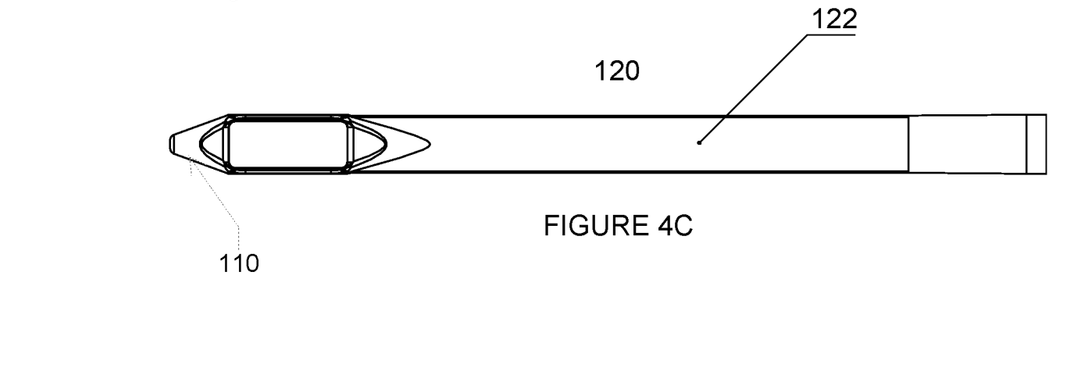
FIG. 4C shows a detailed bottom view of the spring portion of the device.

FIGS. 4A-4C show in more detail the features of the spring (120) of the apparatus (100) of the present invention. FIG. 4A shows a side view of the apparatus (100) with the spring (12) in a relaxed, un-tensioned, state, while FIGS. 4B and 4C show enlarged side and bottom views of the spring (120) with the cleaning tip (110) attached thereto. As shown in FIG. 4A, the spring (120) extends from the distal end of the elongate rod (102) and curves away from the longitudinal axis of the shaft at about 40 to 90 degrees.

FIGS. 4B and 4C show detailed features of the spring (120). Desirable features of the spring are that it allow the cleaning tip (110) to deform preferentially in one direction (on-axis) while remaining as stiff as possible in other directions (off-axis). To accomplish off-axis stiffness, the spring width (122) is as wide as possible, typically limited by the Trocar internal dimension (5 to 15 mm). High off-axis stiffness facilitates endoscope tip cleaning by allowing the cleaning tip's cleaning surface to remain relatively stable when contact with the endoscope tip is made.

On-axis flexibility allows for insertion through a Trocar and also allows for the cleaning surface angle to be altered through contact with the endoscope tip in vivo to better align the cleaning tip to be perpendicular to the endoscope tip. On-axis flexibility is accomplished by thinning the dimension of the spring (121) relative to the spring width (122). As shown in FIGS. 4B and 4C, the spring (120) has a thickness that is substantially smaller than the width of the spring, which allows for preferential bending of the spring in a direction normal to the axis of the shaft. In the present embodiment, a small tip force, preferably no more than 0.75 lbs, is needed to bend the spring (120) into a substantially straight position. In some illustrative embodiments, the spring (120) has a thickness (121) of 2-3 mm. The length of the spring (120) is 50-200 mm. An exemplary spring (120)

used in the apparatus (100) of the present invention has a width of around 9 mm, a thickness of about 2.5 mm and a length of about 95 mm. These dimensions of the spring (120) may be varied in other examples.

The spring (120) may be implemented in stainless steel, or other suitable metals, or using biocompatible injection molded plastics such as polypropylene, polycarbonate, or polystyrene. Beam flexure strengths are a function of the cube of the beam width normal to the bend direction. Plastic flexural modulus of 1000 Mpa or more allow a 2.5 mm thick by 9 mm wide by 95 mm long plastic spring to deform in the on-axis direction into a fully axial position (suitable for Trocar insertion) with only 0.75 lbs of force on the tip. This low force allows easy insertion through a Trocar, and also allows for tip angle modification (relative to the endoscope) in vivo with only light pressure by the endoscope tip. Light pressure on the endoscope tip is required to prevent endoscope tip damage. Off-axis stability, due to the large ratio of spring width to thickness, will be significantly higher than on-axis positional stability. High off-axis stability allows for easy endoscope tip cleaning due to a positionally stable sponge location.

Suitable injection molded plastic properties of >1000 Mpa flexural modulus and >50 Mpa of Flexural Strength can be used for the spring (120) and will create a spring structure utilizing plastic material that satisfies device requirements. Such plastic materials are also suitable for the handle (130), the elongated rod (102) and the cleaning tip (110), enabling the simplest implementation of the device to be predominantly created from a single injection molded plastic part which is then attached to a cleaning surface such as a sponge. This single part plastic implementation satisfies the criteria for a low-cost in vivo endoscope tip cleaning device. Such a device can be single use and disposable. Such a device can be recyclable with the selection of suitable plastic and sponge materials.

Figure 5A:
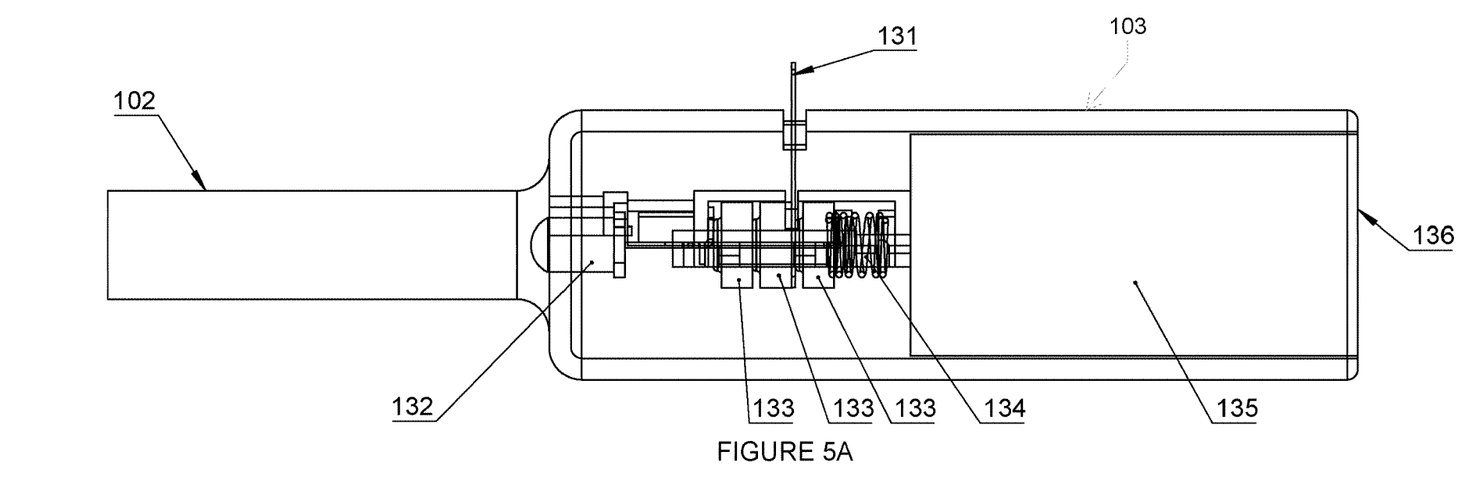
FIG. 5A shows an internal structure side view of the handle containing a light source, batteries powering the light source, and an activation tab for the light source.
Figure 5B:
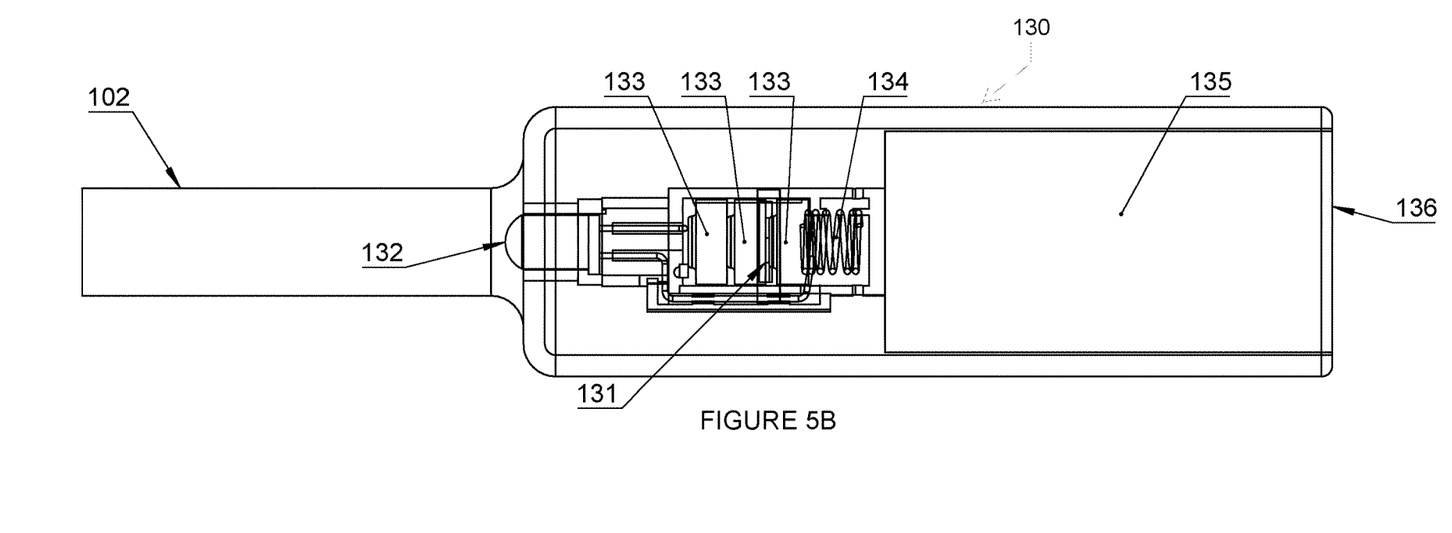
FIG. 5B shows an internal structure bottom view of the handle of the endoscope lens cleaning apparatus of FIG. 5A.

In another implementation, an illumination assembly may be included in the apparatus (100) so that a light is used to illuminate the cleaning tip (110) surrounding the sponge (103). This tip illumination can facilitate the location of the sponge when the endoscope tip is contaminated and limits physician visualization. FIGS. 5A and 5B show an illumination assembly built into the handle (130) of the apparatus (100). The illumination assembly includes a light source (132), such as an LED, a power source (133), such as one or more batteries, and an activation device or switch (131), such as a pull tab, a button or a slide switch. In one illustrative embodiment, the elongated rod (102) and/or the spring (120) and/or the cleaning tip (110) are formed from transparent or translucent plastic or polymer material. In certain embodiments, the handle (130), the elongated rod (102) and the spring (120) are formed by injection molding from a transparent or translucent polymer.

In the embodiment of FIGS. 5A and 5B, the LED (132) directs light into the clear plastic elongated rod (102), which transfers the light via total internal reflection (TIR) to the spring (120) and then into the cleaning tip (110). This light will escape from the cleaning tip (110) causing the cleaning tip (110) to glow on all surfaces that surround the sponge (103). This glow surrounding a dark area will facilitate location of the sponge in vivo by the physician when the endoscope tip is contaminated.

As shown in FIGS. 5A and 5B, the LED (132) is provided at the distal end of the handle (130) and may be at least partially enclosed by the handle (130) and partially enclosed by the proximal end of the elongated rod (102). In other embodiments, the LED may be provided wholly within the handle (130) or may be provided externally to the handle (130) such as within the elongated rod (102). For example, in some embodiments, the LED (132) may be provided at or near the proximal end of the elongated rod (102), and in other embodiments, the LED (132) may be provided at or near the distal end of the elongated rod (102), and in either of these embodiments, the LED (132) is connected to the power source (133) using suitable wiring. In yet other embodiments, the LED (132) may be provided on or inside the cleaning tip (110) and connected to the power source (133) using wiring, which may be attached to or encapsulated within the spring (120) and the elongated rod (102).

As shown, the LED (132) is powered by one or more batteries (133) housed within the handle (130). The one or more batteries can be held in place within the handle (130) or within a chamber formed in the handle (130) by a battery spring (134). Such a battery spring can also make electrical contact on one side of the battery spring to one LED lead and on another side of the battery spring to the one or more batteries. The battery spring may also push the one or more batteries against a second LED lead, thus creating a complete electrical circuit.

In the embodiment of FIG. 5A, the switch (131) is made from an electrically insulating tab, such as a plastic tab, that breaks the electrical circuit when inserted between adjacent batteries (133), and allows the electrical current to flow in the circuit when withdrawn, thus lighting the LED (132). In other embodiments, the switch could also be an electrical slide, toggle, or pushbutton switch which is wired to the circuit. Such slide, toggle, or pushbutton switch could be mounted on the proximal end of the handle (136). However, in other embodiments, the switch (131) may be provided anywhere in the handle (130).

The LED (132), one or more batteries (132), battery spring (134), and switch (131) may be contained in a handle insertion structure (135). This handle insertion structure allows for easy assembly of lighting components into a handle insertion structure, which is then inserted into the proximal end of the handle. The handle insertion structure (135) encloses or partially encloses the batteries (132), the battery spring (134) and may partially enclose the LED (132) and the switch (131). In some embodiments, the handle insertion structure (135) with the illumination assembly may be inserted into the handle (130) through an opening in the proximal end of the handle (130) or an opening in a side of the handle (130).

Figure 6:
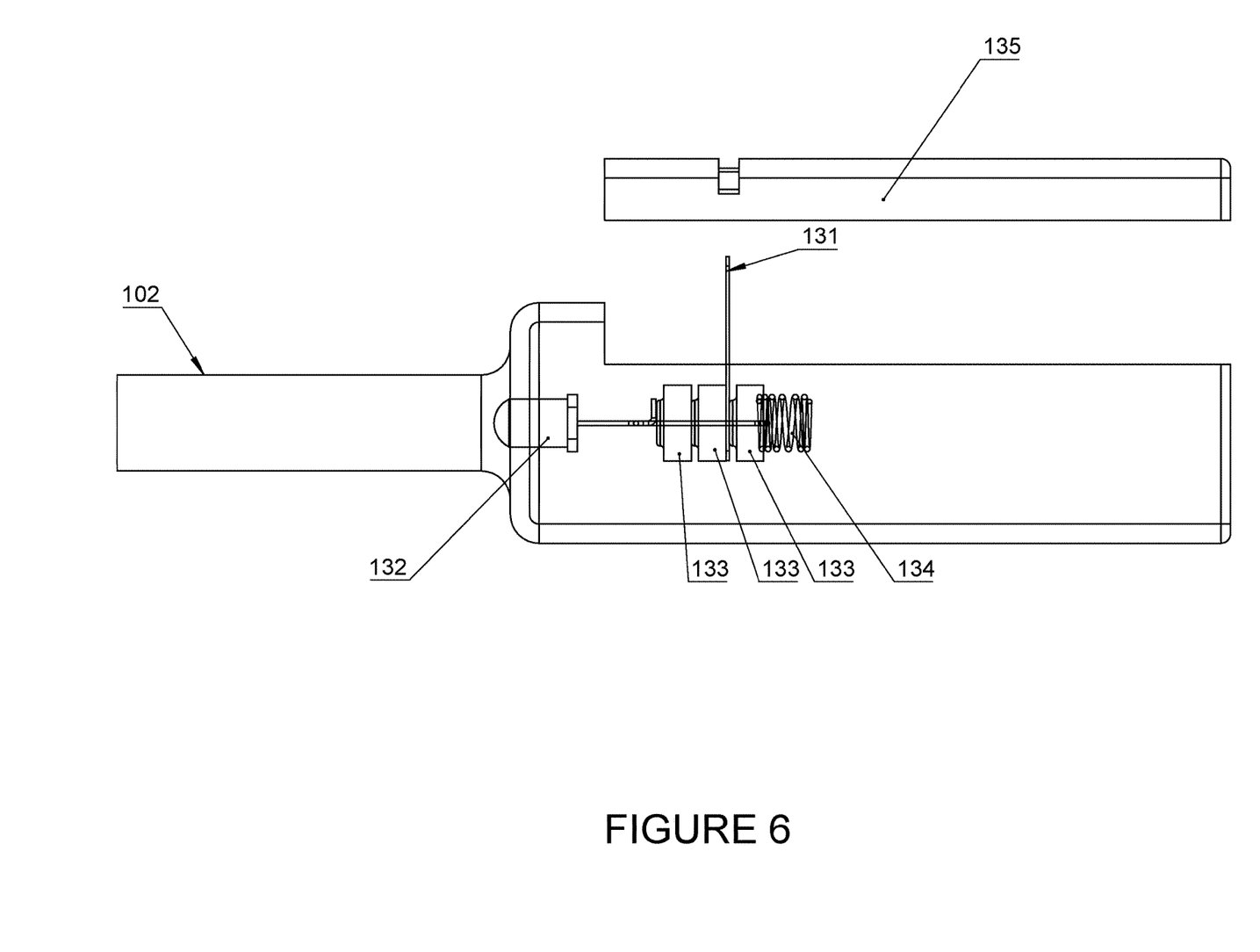
FIG. 6 shows a cross-sectional view of the handle of the device containing features for side access to a lighting assembly build into the handle.

FIG. 6 shows another implementation of a lighting assembly built into the handle (130) directly, without using a separate handle insertion structure. In this implementation, the lighting assembly components, including the LED (132), the one or more batteries (133), the switch (131) and the spring (134) are mounted into molded structures within the handle and a handle door (135) is then assembled onto the handle (130) to contain the lighting assembly. The lighting assembly components are held in place by the internal molded structures of the handle (130) and the handle door (135).

Figure 7:
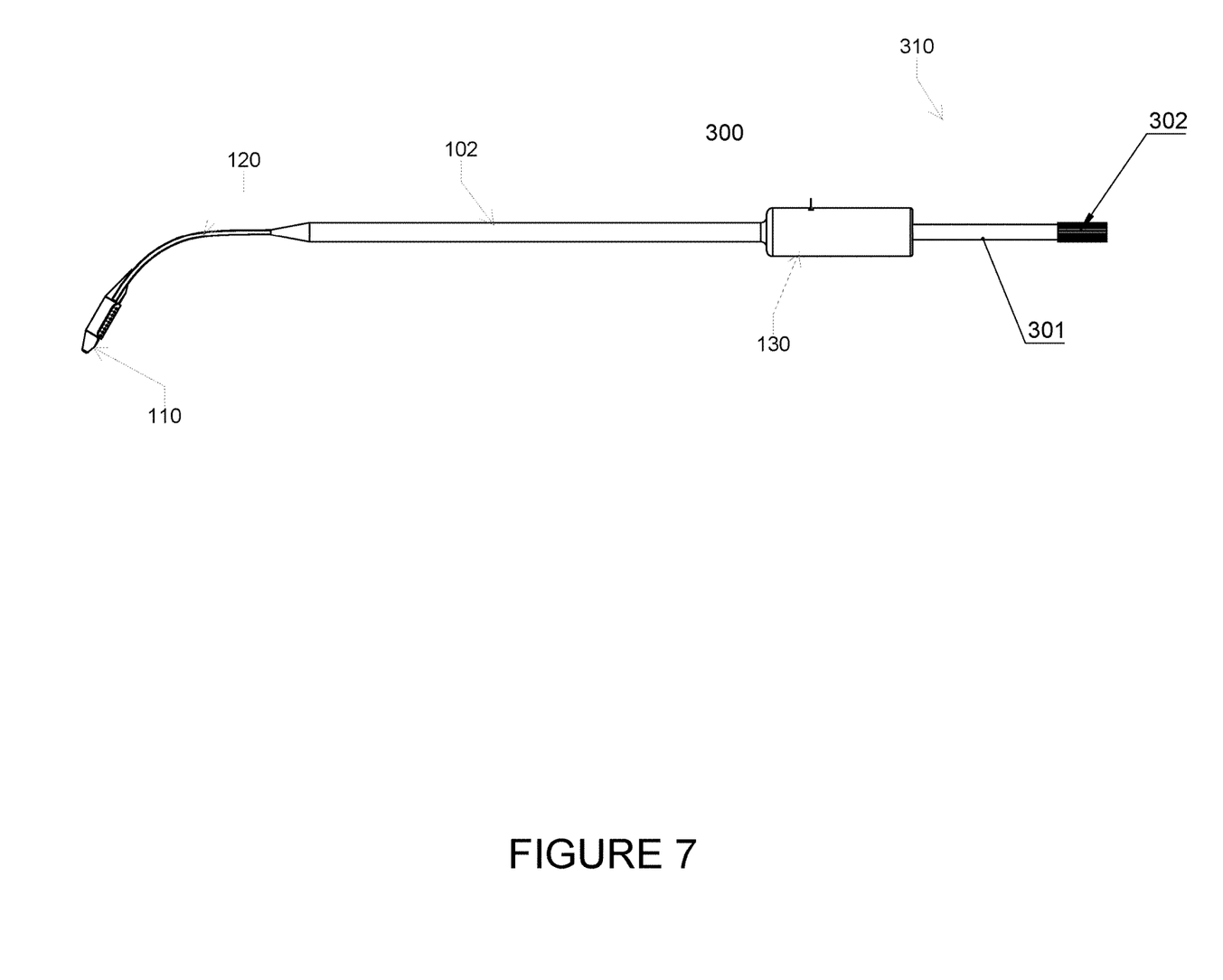
FIG. 7 shows a Trocar cleaning device mounted to the proximal end of the handle of the endoscope lens cleaning apparatus.

Since endoscopes are often inserted through Trocars, and Trocars can become contaminated during surgery, often the endoscope tip will become contaminated and visually impaired upon insertion through a Trocar. The endoscope lens cleaning apparatus of the present invention may be modified to enable cleaning of a Trocar in order to avoid contamination of other instruments used during surgery. FIG. 7 shows an implementation of the modified endoscope lens cleaning apparatus (300) that includes a Trocar cleaning structure (310) attached at the proximal end thereof. This Trocar cleaning structure includes a shaft (301) and cleaning surface (302) mounted to the shaft (301). This cleaning surface (302) can be a sponge or another suitable cleaning surface which is attached by an adhesive, such as glue, epoxy or UV Cure, a mechanical clip, another fastener, or simply stretched over the shaft. The shaft (301) can be attached to the handle (130) via an insertion slot built into the proximal end of the handle (130), via a threaded screw hole in the proximal end of the handle (130), or via any other suitable attachment methods. In other embodiments, the shaft (301) is molded as part of the handle (130) via injection molding techniques or otherwise formed integrally with the handle (130).

The above-described implementations of the apparatus (100, 300) show that a surgeon can leave the endoscope in the abdominal cavity and clean the tip of the endoscope using this apparatus (100, 300) without having to withdraw and replace the endoscope. The apparatus (100, 300) may be retracted from, and reinserted through the trocar tube at any point in the surgery without the need to retract the endoscope. When inserted through the Trocar, the cleaning tip (110) of the apparatus may be oriented so that it does not obstruct the surgical field, so that it is in position for subsequent cleaning of the optical lens of the endoscope. Upon completion of the surgical procedure, or if changing of the cleaning pad (103) is required, the apparatus (100, 300) is withdrawn from the trocar tube. When Trocar cleaning is required, the apparatus (100, 300) may be extracted from the Trocar and used to clean the Trocar, which may subsequently be used for endoscope insertion. To aid the physician in locating the endoscope tip to the sponge (103) of the apparatus (100, 300), a contrasting sponge color, such as green, may be used. Additional aid to the physician in locating the endoscope tip to the sponge (103) of the apparatus (100, 300) can be provided by an illumination assembly that illuminates the cleaning tip (110) of the apparatus (100, 300) surrounding the sponge (103).

As will be appreciated with the benefit of the present disclosure, the apparatus of the present invention can effectively clean the tip of the laparoscope or endoscope in vivo, without need for any tubing or connections, eliminating the need to withdraw the laparoscope or endoscope, maintaining full visualization of the operative field, and can therefore increase patient safety while reducing operative time. These benefits can be realized via low cost injection molded plastic techniques and assembly techniques that can be as simple as attaching two or more components together.

The apparatus is formed of materials that will withstand sterilization, such as by gamma irradiation, ETO, or other methods, prior to use in patients. In some embodiments, the apparatus is placed within a delivery system that allows for deployment and retraction of the apparatus to facilitate insertion and removal.

Figure 8:
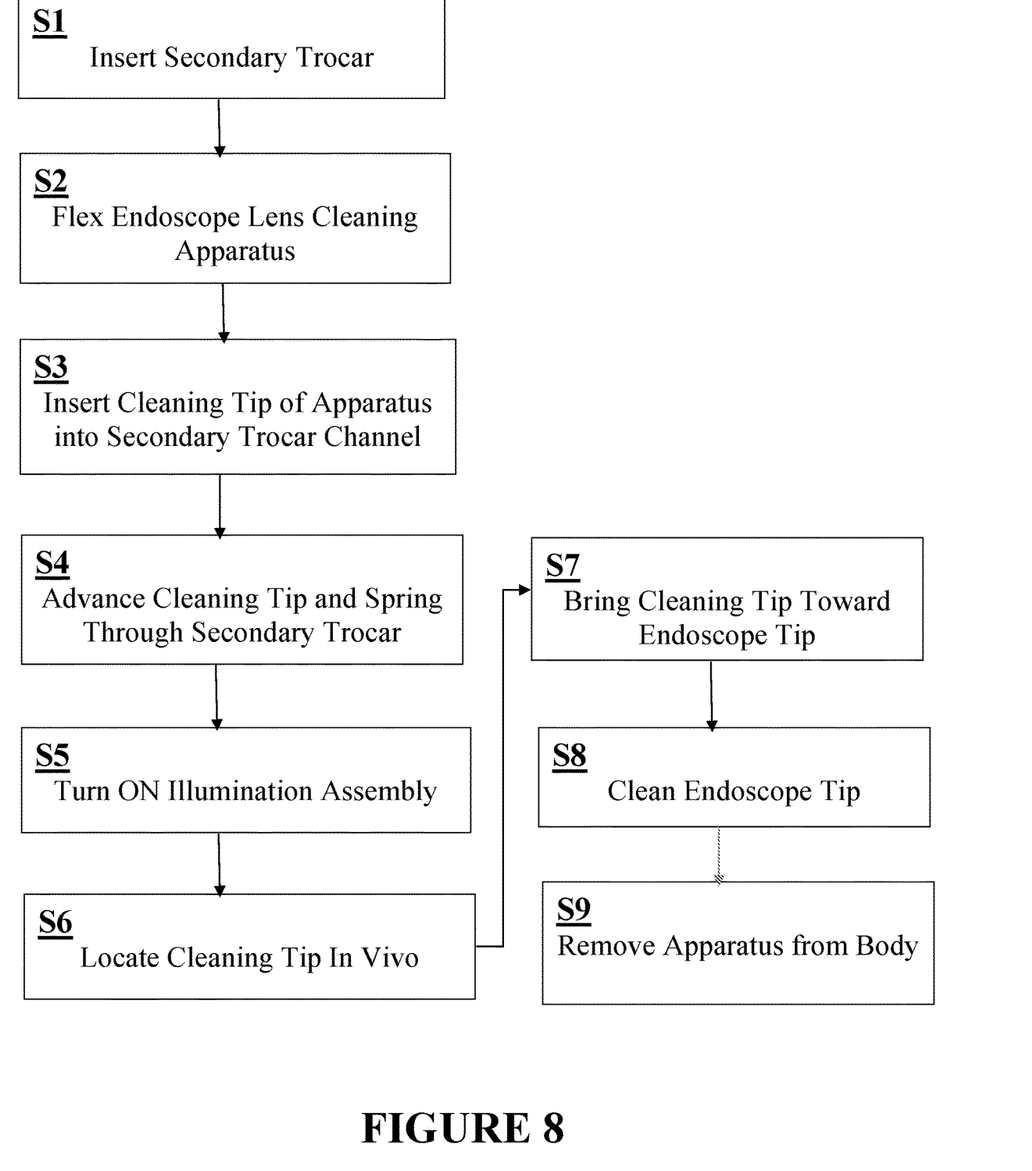
FIG. 8 shows an exemplary method of cleaning the endoscope tip using the device of the present invention.

The endoscope lens cleaning apparatus (100) described above may be used in a method of cleaning an endoscope lens tip in vivo. FIG. 8 shows an illustrative method of cleaning the endoscope lens tip inside a human body. The method assumes that a primary trocar is used for the endoscope inserted into a body of a patient. However, the method steps would be the same or substantially the same if the endoscope is inserted into the body via one of the secondary trocars.

In step S1 of the method of FIG. 8, a secondary trocar is inserted through an incision into the body of a patient a predetermined distance away from the primary trocar used for the endoscope. The predetermined distance is typically about 6-10 cm, depending on the patient and the type of surgery. In step S2, the endoscope lens cleaning apparatus (100) is flexed so that the spring (120) is in a substantially straight alignment with the elongated rod (102).

In step S3, the cleaning tip 110 is inserted into the channel of the secondary trocar and in step S4, the cleaning tip (110) and the spring (120) are advanced through the secondary trocar channel into the body. If the apparatus (100) includes an illumination assembly, in step S5, the illumination assembly is activated to turn on the light source by removing the tab switch or by turning ON the activating switch.

In step S6, the cleaning tip (110) of the apparatus is located within the body using the endoscope and in step S7, the handle (130) of the apparatus is manipulated to bring the cleaning tip (110) toward the tip of the endoscope while observing the cleaning tip (110) using the endoscope. In step S8, the cleaning pad (103) on the cleaning tip (110) of the apparatus (100) is brought into contact with the endoscope tip so as to apply gentle pressure to the endoscope tip and to clean any fluids and/or debris from the endoscope tip. After the cleaning of the endoscope tip is completed, in step S9, the apparatus (100) may be removed from the body via the secondary trocar.

The method of FIG. 8 may be modified so as to perform multiple cleanings of the endoscope tip without removing the apparatus (100) from the body. In addition, the method may include an additional step of applying anti-fog cleaning solution to the cleaning pad (103) either prior to insertion of the apparatus (100) into the trocar channel or in vivo.

It should be understood, of course, that the foregoing relates to exemplary embodiments of the invention and that modifications may be made without departing from the spirit and scope of the invention. Although certain embodiments have been described in considerable detail herein, other embodiments, variations, and modifications that fall within the spirit and scope of the invention will be apparent to those skilled in the art. Therefore, the scope of any claims allowed for this application should not be limited to any specific embodiments or to any non-claimed details of the embodiments described herein.

What is claimed:

1. A surgical device comprising: a shaft having a first cross-sectional shape and having a proximal end and a distal end; a spring having a second cross-sectional shape different from the first cross-sectional shape and extending distally from the distal end of the shaft and curving away from a longitudinal axis of the shaft, the spring having a predetermined width and a first thickness substantially smaller than the predetermined width to provide preferential bending in a direction of the curvature of the spring, and a tip extending from a distal end of the spring, said tip having a second thickness and including an attachment surface for attaching an absorbent material thereto, wherein a proximal end of the tip gradually tapers from the second thickness to the first thickness of the spring, wherein the second thickness is greater than the first thickness, and wherein the surgical device is a cleaning device configured to clean a lens of a surgical visualization device.

2. The surgical device of claim 1, further comprising the absorbent material configured to attach to the attachment surface of the tip, wherein the absorbent material comprises one of a sponge, a cloth, a cleaning pad and a plastic foam.

3. The surgical device of claim 2, wherein the absorbent material has a contrasting color to a patient surgical cavity.

4. The surgical device of claim 1, wherein the shaft includes a handle formed at the proximal end thereof.

5. The surgical device of claim 4, wherein the tip, the spring, the shaft, and the handle are integrally formed into a single structure.

6. The surgical device of claim 5, wherein the single structure is molded from a biocompatible plastic.

7. The surgical device of claim 6, wherein the biocompatible plastic is transparent and wherein the surgical device further comprises an illumination assembly at least partially housed within the handle, said illumination assembly configured to provide light to the tip through the shaft and the spring via total internal reflection.

8. The surgical device of claim 1, wherein the shaft has a third thickness, and the distal end of the shaft gradually tapers from the third thickness to the first thickness of the spring.

9. The surgical device of claim 1, wherein the tip includes:
a conical distal end,
one or more ramps providing a smooth transition between the spring and a body of the tip; and
a recess in the body of the tip, said attachment surface being provided in said recess.

10. The surgical device of claim 1, where a tip force of no more than 0.75 lbs is required to bend the spring into a straight position aligned with the longitudinal axis of the shaft.

11. The surgical device of claim 1, wherein the tip, the spring, and the shaft are integrally formed into a single structure.

12. The surgical device of claim 1, further comprising a second shaft attached to the proximal end of the surgical device, and a second absorbent material attached to a free end of the second shaft.

13. The surgical device of claim 1, wherein the spring curves 40-90 degrees away from the longitudinal axis of the shaft.

14. The surgical device of claim 1, wherein the tip forms a free end of the surgical device.

15. A method of wiping a tip of a visualization device inside a human body comprising: inserting a surgical device into the human body separately from the visualization device via an incision, the surgical device comprising a shaft, a spring extending from a distal end of the shaft and curving away from a longitudinal axis of the shaft, a tip extending from the distal end of the spring and including an attachment surface, and an absorbent material attached to the attachment surface of the tip, manipulating the surgical device so that the absorbent material attached to the tip of the surgical device comes into contact with the tip of the visualization device, and applying pressure to the tip of the visualization device using the tip of the surgical device so as to wipe the tip of the visualization device using the absorbent material, wherein in the inserting step, the surgical device is inserted through an insertion channel, and wherein a proximal end of the tip gradually tapers from a second thickness of the tip to a first thickness of the spring, wherein the second thickness is greater than the first thickness, so that in the inserting step, insertion impediments caused by temporary interfacing between the tip and the insertion channel are reduced.

16. The method of claim 15, wherein inserting the surgical device into the human body comprises flexing the spring of the surgical device so that the spring is substantially aligned with the longitudinal axis of the shaft and inserting at least the tip and the spring of the surgical device through a trocar inserted into the human body via a secondary incision a predetermined distance away from a primary incision for inserting the visualization device, and wherein after the surgical device is inserted into the human body, the spring returns to a relaxed state curving away from the longitudinal axis of the shaft.

17. The method of claim 16, further comprising removing the surgical device from the human body by passing at least the spring and the tip of the surgical device through the trocar to the outside of the body, wherein during the removing step, the spring is flexed to be substantially aligned with the longitudinal axis of the shaft.

18. The method of claim 15, wherein a proximal end of the shaft is attached to a handle and the step of manipulating is performed by manipulating the handle.

19. The method of claim 15, wherein the surgical device includes an illumination assembly configured to provide light to the tip of the surgical device, and the method further comprises illuminating the tip of the surgical device to enhance visibility of the tip in the human body.

20. The method of claim 15, further comprising attaching the absorbent material to the attachment surface of the tip prior to the inserting step.

21. The method of claim 15, further comprising applying cleaning solution to the absorbent material, said step of applying is performed one of (a) ex vivo prior to the inserting step, and (b) in vivo after the inserting step.

22. A surgical device comprising: a shaft having a proximal end and a distal end; spring having a first thickness and including a proximal portion extending from the distal end of the shaft along a longitudinal axis of the shaft and a distal portion following the proximal portion and gradually curving to 40 to 90 degrees away from a longitudinal axis of the shaft, and a tip extending from a distal end of the spring, said tip having a second thickness and having an attachment surface for attaching an absorbent material thereto, wherein, when the surgical device is inserted through an insertion channel, the spring is configured to independently deform from an initial curved position to a second position that is colinear to the insertion channel, wherein a proximal end of the tip gradually tapers from the second thickness to the first thickness of the spring, wherein the second thickness is greater than the first thickness, and wherein the surgical device is a cleaning device configured to clean a lens of a surgical visualization device.

23. The surgical device of claim 22, wherein the shaft has a third thickness, and the distal end of the shaft gradually tapers from the third thickness to the first thickness of the spring.

24. The surgical device of claim 22, wherein the tip includes a conical distal end, one or more ramps providing a smooth transition between the spring and a body of the tip, and a recess in the body of the tip, said attachment surface being provided in said recess.

25. The surgical device of claim 24, wherein sidewalls of the body of the tip adjacent the recess are curved into the recess.

26. The surgical device of claim 22, further comprising the absorbent material configured to attach to the attachment surface, wherein the absorbent material is one of a sponge, a cloth, a cleaning pad and a plastic foam.

27. The surgical device of claim 22, further comprising a handle provided at the proximal end of the shaft.

28. The surgical device of claim 22, wherein the spring is configured so as to preferentially bend in a direction of the curvature of the spring and to resist bending around the longitudinal axis of the shaft.

29. The surgical device of claim 22, further comprising an illumination assembly including one or more light sources, one or more power sources and an activation switch for activating the illumination assembly, wherein the illumination assembly provides illumination to the tip of the surgical device.

30. The surgical device of claim 29, further comprising a handle extending from the proximal end of the shaft and wherein:
- at least the shaft, the spring and the tip are formed from a transparent or translucent material,
- at least a portion of the illumination assembly is enclosed by the handle, and
- light emitted from the light source of the illumination assembly is transmitted through the shaft and the spring to the tip by total internal reflection.

31. The surgical device of claim 22, further comprising a second shaft attached to the proximal end of the surgical device, and a second absorbent material attached to a free end of the second shaft.

* * * * *

UNITED STATES PATENT AND TRADEMARK OFFICE
CERTIFICATE OF CORRECTION

| | | |
|---|---|---|
| PATENT NO. | : 11,154,187 B2 | |
| APPLICATION NO. | : 16/819483 | |
| DATED | : October 26, 2021 | |
| INVENTOR(S) | : Peter H. Kwon, James D. Levinsohn and Jeffrey Ralph Swift | |

It is certified that error appears in the above-identified patent and that said Letters Patent is hereby corrected as shown below:

On the Title Page

Item (71) Applicants, delete:
"(71) Applicants: Peter H. Kwon, Middletown, NY (US);
James L. Levinsohn, Middletown, NY (US); Jeffrey Ralph Swift, Boca Grande, FL (US)"

And insert:
--(71) Applicants: Peter H. Kwon, Middletown, NY (US);
James D. Levinsohn, Middletown, NY (US); Jeffrey Ralph Swift, Boca Grande, FL (US)--

Item (72) Inventors, delete:
"(72) Inventors: Peter H. Kwon, Middletown, NY (US);
James L. Levinsohn, Middletown, NY (US); Jeffrey Ralph Swift, Boca Grande, FL (US)"

And insert:
--(72) Inventors: Peter H. Kwon, Middletown, NY (US);
James D. Levinsohn, Middletown, NY (US); Jeffrey Ralph Swift, Boca Grande, FL (US)--

Signed and Sealed this
Sixteenth Day of August, 2022

Katherine Kelly Vidal
*Director of the United States Patent and Trademark Office*